United States Patent [19]

Angier et al.

[11] 4,089,965

[45] May 16, 1978

[54] THIAZOLYLPHENYLGUANIDINES AS ANTIRHINOVIRUS AGENTS

[75] Inventors: Robert Bruce Angier; Harry Lee Lindsay, both of Pearl River, N.Y.

[73] Assignee: American Cyanamid Company, Stamford, Conn.

[21] Appl. No.: 798,201

[22] Filed: May 18, 1977

Related U.S. Application Data

[63] Continuation-in-part of Ser. No. 670,761, Mar. 26, 1976, abandoned.

[51] Int. Cl.$^2$ ............................................. A61K 31/425
[52] U.S. Cl. ..................................................... 424/270
[58] Field of Search .......................................... 424/270

[56] References Cited

PUBLICATIONS

Beyer et al., Chem. Ber. 99, pp. 2931–2943 (1966).
McKee et al., J. of Organic Chem. 17, pp. 1494–1496 (1952).
Chemical Abstracts 80:104407f (1974).
The Merck Manual, 12 ed., 1972, Merck & Co., Inc., Rahway, N.J., p. 19, table 2.

*Primary Examiner*—Jerome D. Goldberg
*Attorney, Agent, or Firm*—Norton S. Johnson

[57] ABSTRACT

Methods of treating rhinovirus infections, employing substituted thiazolyl phenylguanidines are described.

8 Claims, No Drawings

THIAZOLYLPHENYLGUANIDINES AS ANTIRHINOVIRUS AGENTS

CROSS-REFERENCE TO RELATED APPLICATIONS

This application is a continuation-in-part of our co-pending application Ser. No. 670,761 filed Mar. 26, 1976, now abandoned, which, in turn, claimed the benefit of the filing date of the British Provisional application Ser. No. 13,567 filed Apr. 2, 1975.

PRIOR ART

The compound 1-(4-phenyl-2-thiazolyl) 3-phenylguanidine and derivatives are described in the following references: 1) H. Beyer and K. Pommerening, Chem. Ber. 99, 2931–2943 (1966), 2) R. L. McKee and J. D. Thayer, Journal of Organic Chemistry 17, 1494–1496 (1952). Also the German Pat. No. 2,132,431 describes antiviral (but not antirhinoviral) activity for related thiazolylurea and thiazolylthiourea compounds.

DESCRIPTION OF THE INVENTION

This invention relates to methods for preventing or treating rhinovirus infections. In particular, this invention consists of methods of inhibition of the growth of the common cold virud (rhinovirus) with pharmaceutical compositions containing a substituted thiazolyl phenylguanidine and a pharmaceutical carrier.

The thiazolylphenylguanidines which are useful in the treatment of rhinovirus infections may be described by the following formula:

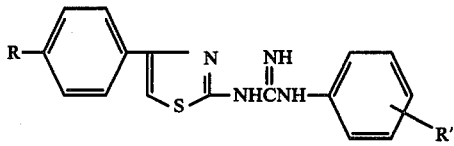

wherein R is hydrogen or chloride and R' is hydrogen, fluoride, chloride, lower alkyl, carboxyl or carboloweralkoxy. The lower alkyl and lower alkoxy groups are those having 1 to 4 carbon atoms.

Also included within the scope of the invention are methods of employing the pharmaceutically acceptable acid addition salts of the compounds of the above formula. Among these salts are the hydrochloride, sulfate, nitrate, hydrobromide, maleate, tartrate and benzoate. These salts are prepared in the conventional manner by reacting the base compounds with an acid to form the corresponding acid addition salt.

The active components of this invention are prepared according to the following method:

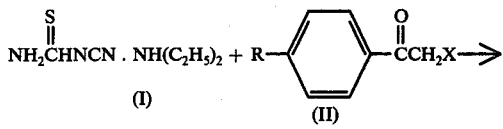

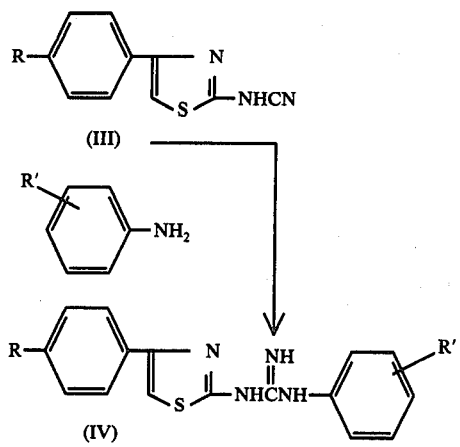

wherein R and R' are as hereinbefore described.

The diethylamine salt (I) of N-cyanothiourea (McKee et al. described above) is treated with an α-haloacetophenone (II) in refluxing methanol to give a 4-phenyl-2-thiazolylcarbamonitrile (III) which is then reacted with aniline or a substituted aniline derivative in refluxing ethanol to yield the 1-(4-phenyl-2-thiazolyl)-3-phenylguandine or substituted derivative (IV).

The compounds described, as well as their pharmaceutically acceptable acid addition salts, may be formulated into compositions for use as antirhinoviral agents by methods well known in the skilled pharmaceutical chemist. When compositions are intended to be administered orally, preferably in the form of a tablet or capsule, they can be pepared in the usual manner or formulated into a sustained release preparation by methods well known in the art. Another preferred mode of administration is by intranasal application, preferably in the form of a suspension or solution which is sprayed into the nasal tissue. A further form of administration can be by intramuscular or subcutaneous injection. The intranasal formulation is best administered as a 0.5–10% suspension in the form of a spray or nose drops, several times a day. The injectable formulation is administered once at a concentration of 0.5 to 2.0 mg./kg. of body weight.

The compositions are preferably administered to a warm-blooded animal prior to rhinovirus infection in order to prevent or ameliorate the infection, soon after known exposure to infection or upon recognition of symptoms in order to treat the infection and minimize its systemic effects.

The compounds of the present invention are active *in vitro* against a variety of viruses causing respiratory illness such as the "common cold" or rhinovirus.

Confluent monolayers of a continuous cell-line such as HeLa, HEp-2, KB or L-132, grown in plastic tissue culture dishes, were infected with one of the rhinoviruses, for example, types 1B, 2, 5, 14 or 23 and other members of the picornavirus group, including the enteroviruses, for example, coxsackie A-11 and A-21.

Protection of the tissues to the cytopathic effects of the viruses were ascertained either by means of a plaque inhibition test in which the test compound was adsorbed onto a filter paper disc and placed on the agar used to overlay the infected cell monolayers, or by incorporation into the said agar overlay. The agar overlay medium used for this purpose was of the following formulation:

| Minimum Essential Medium (Eagle) containing Earle's salts (Grand Island Biological Co., Grand Island, N.Y.) and to which has been added | |
| --- | --- |
| Ionagar No. 2 | 0.4% |
| Diethylaminoethyl dextran | 0.01% |
| Magnesium chloride | 0.06% |
| Fetal calf serum | 2.0% v/v |

The virus infected cell monolayers plus test compound were incubated in a humidifier atmosphere of 5% carbon dioxide at 33° for 3 to 5 days. The ability of these compounds to protect tissues from destruction by the viruses was then evident after staining the residual uninfected cells with 0.5% crystal violet in 20% ethanol. The results appear in Table I.

TABLE I

| Compound | Rhinovirus strains | | | | |
| --- | --- | --- | --- | --- | --- |
| | 2 | 5 | 14 | 23 | 1B |
| 1-(4-Phenyl-2-thiazolyl-3-phenylguanidine | + | + | + | + | ∓ |
| 1-(4-Phenyl-2-thiazolyl)-3-(3-chlorophenyl)-quanidine | + | | | | |
| 1-(4-Phenyl-2-thiazolyl)-3-(4-carbomethoxy)-phenylguanidine | + | | | + | ∓ |
| 1-(4-Phenyl-2-thiazolyl)-3-(p-tolyl)guanidine | + | + | + | + | + |
| 1-(4-Phenyl-2-thiazolyl)-3-(4-fluorophenyl)-guanidine | + | + | | | + |
| 1-(4-Phenyl-2-thiazolyl)-3-(4-carboxyphenyl)-guanidine | + | + | + | + | + |
| 1-[4-(4-Chlorophenyl)-2-thiazolyl]-3-(p-tolyl)guanidine | + | | | + | |

+ = Protects tissue from destruction by virus
∓ = Partial protection

In plaque assays, to determine the minimal inhibitory concentration (MIC), 1-(4-phenyl-2-thiazolyl-3-phenylguanidine was dissolved in dimethylsulfoxide or polyethylene glycol 400 or was homogenized in culture medium at 100–250 mg/ml. Two-fold, serial dilutions were prepared in culture medium or in the respective solvent and aliquots of each dilution were incorporated in the culture overlay medium at the desired drug concentration. When the drug was dissolved in solvent, a final, constant concentration of dimethylsulfoxide at 0.04% or polyethylene glycol 400 at 0.2% was present in the culture overlay medium.

To determine the MIC (that concentration of drug inhibiting virus plague formation by 50%), plague tests were performed on HeLa cells infected with 100–300 plague-forming units of rhinovirus, poliovirus or coxsackievirus. Following virus adsorption, 10 ml. of agar overlay medium containing 1-(4-phenyl-2-thiazolyl)-3-phenylguanidine was added to each dish. Cultures infected with rhinovirus were incubated at 33° C. for 4 to 5 days. Poliovirus and coxsackievirus-infected cultures were incubated at 37° C. for 2 to 4 days. Uninfected cultures with drug and cultures with dimethylsulfoxide or polyethylene glycol 400 only were included as controls in the tests. At the end of the incubation period, cultures were stained with 0.1% crystal violet in 20% ethanol and the plagues were counted. The results appear in Table II.

TABLE II

| Virus | | Minimal Inhibitory Concentration (mcg/ml) | | |
| --- | --- | --- | --- | --- |
| | | HeLa Cells | L-132 Cells | Detroit-6 Cells |
| Rhinovirus Serotype | 1A | 0.2–0.4 | | |
| | 1B | 0.8–1.6 | 0.8 | |
| | 2 | 0.4–0.8 | 0.4–0.8 | 0.4 |
| | 3 | 0.4–0.8 | | |
| | 5 | 0.4–0.8 | | |
| | 12 | 0.2–0.4 | | |
| | 14 | 0.8–1.6 | | |
| | 20 | 0.4 | | |
| | 23 | 0.2–0.4 | 0.4–0.8 | |
| | 32 | 0.4 | | |
| | 39 | 0.4 | | |
| | 50 | 0.2–0.4 | | |
| | 52 | 0.4 | | |
| Coxsackievirus | A-5 | 0.4 | | |
| | A-11 | 1.6–3.1 | | |
| | A-15 | 1.6–3.1 | | |
| | A-21 | 1.6–3.1 | | |
| | A-22 | 1.6–3.1 | | |
| | B-1 | 1.6–3.1 | | |
| | B-2 | 0.8–1.6 | | |
| | B-5 | 0.8–1.6 | | |
| Poliovirus | Type 1 | 0.8 | | |

In the test for viral sensitivity, by the filter disc method, 5 mg. of 1-(4-phenyl-2-thiazolyl)-3-phenylguanidine was dissolved in 1–2 drops of dimethylsulfoxide and 2.5 ml. of saline. Filter paper discs, when saturated with the solution, absorbed about 50 mcg. of the compound.

Sensitivity tests were performed by a modification of the method of Herrmann, et al., Proc. Soc. Exp. Biol. & Med., 103, 625 (1960). HeLa monolayers in 150 mm plastic dishes were infected with 1.0 ml. of rhinovirus suspension known to produce destruction of 80–90% of the cells in 4 to 5 days. Following viral adsorption, the cells were overlayed with 30 ml. of Eagle's minimum essential medium containing Noble agar at 0.5%, bovine fetal serum at 2.0%, diethylaminoethyl dextran at 100 mcg/ml. and magnesium chloride at 3 millimoles. Filter discs (1/4 inch Carl Schleicher and Schuell Co., No. 740E), containing about 50 mcg. of 1-(4-phenyl-2-thiazolyl)-3-phenylguanidine, were placed on the solidified surface and the culture plates incubated at 33° C. After 4 to 5 days, the overlay medium was decanted and the cells stained with 0.1% crystal violet in 20% ethanol. A zone of 10 mm or more in which at least two-thirds of the cells were protected from viral cytopathic effects, indicates antiviral activity. The following Table III lists 35 rhinovirus serotypes which were inhibited by this compound.

TABLE III

| Rhinovirus Type | Strain |
| --- | --- |
| 1B | B632 |
| 2 | HGP |
| 4 | 16/60 |
| 5 | Norman |
| 9 | 211CV13 |
| 10 | 204CV14 |
| 11 | 1CV15 |
| 12 | 181CV16 |
| 13 | 353 |
| 14 | 1059 |
| 15 | 1734 |
| 16 | 11757 |
| 19 | 6072CV18 |
| 21 | 47CV21 |
| 22 | 127CV22 |
| 23 | 5124CV24 |
| 24 | 5146CV25 |
| 25 | 5426CV26 |
| 26 | 5660CV27 |
| 28 | 6101CV29 |
| 29 | 179E |
| 30 | 106F |
| 31 | 140F |
| 34 | 137-3 |
| 36 | 342H |
| 38 | CH79 |
| 41 | 56110 |
| 45 | Baylor 1 |
| 46 | Baylor 2 |
| 47 | 1979MCV46 |

TABLE III-continued

| Rhinovirus Type | Strain |
|---|---|
| 49 | 8213 |
| 50 | A2 No. 58 |
| 51 | 605CV45 |
| 52 | 515-CV34 |
| 53 | FO13928 |

Virus Yield Reduction Test

In a test to determine virus yield 1-(4-phenyl-2-thiazolyl)-3-phenylguanidine is incorporated in Eagle's minimum essential medium supplemented with bovine fetal serum at 2.0%. HeLa cell monolayers in 60 mm dishes were exposed to this drug in this medium for 6 hours, during and following infection with rhinovirus serotype 1B at a virus multiplicity of 1. Drug treated and control cultures were washed 3 times and medium without drug was added for the remaining period of incubation. Virus yields were determined by plague assay of culture fluids harvested at 24 and 48 hours after infection. The results of this test, showing significant inhibition of rhinovirus type 1B as indicated by the suppression of 1-2 logs of virus yield at 24 hours in cultures treated with 0.4 to 0.8 mcg/ml. of drug appear in Table IV.

TABLE IV

| Drug Dose mcg/ml | Time of Exposure of Cells to Drug* | Plaque-Forming Units/ml. (Log 10) | |
|---|---|---|---|
| | | 24 Hours | 48 Hours |
| 6.2 | 0 Hour to +6 Hour | 5.8 | 6.1 |
| 3.1 | | 5.5 | 6.1 |
| 1.6 | | 5.5 | 6.2 |
| 0.8 | | 5.7 | 6.3 |
| 0.4 | | 5.2 | 5.8 |
| None | | 7.0 | 7.0 |
| 12.5 | +1 Hour to +7 Hour | 3.8 | 5.2 |
| 6.2 | | 4.5 | 5.6 |
| 3.1 | | 4.7 | 6.3 |
| 1.6 | | 5.4 | 6.6 |
| 0.8 | | 6.0 | 7.4 |
| 0.4 | | 6.4 | 7.1 |
| None | | 7.0 | 7.2 |

*HeLa cells were adsorbed with virus at a multiplicity of 1 at 0 hour for a period of one hour. The drug was initially solubilized in dimethylsulfoxide or polyethyleneglycol 400 and was added during or one hour after virus adsorption, and then removed after 6 hours and the monolayers washed three times with medium.

In addition to the above, compound 1-(4-phenyl-2-thiazolyl)-3-phenylguanidine is active against a broad spectrum of rhinoviruses and other picornaviruses, including coxsackie and poliovirus in human cell cultures. 1-(4-phenyl-2-thiazolyl)-3-phenylguanidine produces concentration-related inhibition of virus growth as determined by inhibitory effects on virus plaque formation and virus yield. The compound is equally active against rhinoviruses in three different human epithelial cell lines (Hela, L-132 and Detroit-6).

Applicants also wish to establish clinical antirhinoviral activity for the subject compounds by setting forth the following protocol and results thereof.

Thirty amber bottles containing 10 ml each of a suspension of 1-(4-phenyl-2-thiazolyl)-3-phenylguanidine in water, polyethylene glycol and other excipients at a concentration of 250 mg/ml and coded for volunteers No. 3, 4, 6, 7, 9, 10, 13, 14, 17 and 20 as well as thirty amber bottles containing a solution of polyethylene glycol, water and the same excipients and coded for volunteers No. 1, 2, 5, 8, 11, 12, 15, 16, 18 and 19.

Serum specimens were collected from 50 adult male humans between the ages of 18 and 55. These specimens were titrated for neutralizing anitbody against the challenge rhinovirus 32. From these, 25 sero-negative subjects (antibody titer < 1:2) were examined and tested by chest X-ray, electrocardiogram, CBC, blood chemistry, urinalysis, etc. Of these 25, 20 healthy men who were free of allergic, hepatic, renal, immunologic, cardiac, gastrointestinal, metabolic, CNS and hematopietic disease were selected for the study.

The 20 participants were confined as inpatients for 4 days prior to the viral challenge and for 10 days post-challenge. They were outpatients for the follow-up evaluations (days 14, 21, and 28 post-challenge).

The duration of therapy for each subject was 7 and ½ days for each treatment group which consisted of 10 subjects. Each subjects received one day of test medication and one dose (at 8:00 AM on the day of challenge) prior to intranasal viral challenge and 2 doses (1:00 PM and 6:00 PM on the day of challenge) and 5 days of test medication thereafter. On day 6, the subjects received one dose of test medication at 8:00 AM.

The challenge rhinovirus 32 is a second passage virus in WI-38 cell culture. The inoculum contains, in addition to rhinovirus 32, minimum essential medium with Earle's balanced salt solution, 2% fetal calf serum, penicillin (200 units/ml) and streptomycin (200 mcg/ml). The inoculum has been shown to contain no adventitious micro-organisms.

The challenge inoculum was administered by nose drops on the second day of medication about 2 hours after the first dose of test drug. The inoculum was diluted to contain approximately 100 $TCID_{50}$/ml of the challenge dose. Each subject received 0.5 ml of the virus inoculum into each nostril while lying supine across a bed with his neck hyperextended at the edge of the bed. As the inoculum was administered to each nostril, using one ml tuberculin syringes with the needle detached, the subject occluded the other nostril and sniffed gently. Each subject remained in a supine position for at least one minute and refrained from blowing his nose for at least 15 minutes.

Each group of 10 subjects received doses from either the samples coded 3, 4, 6, 7, 9, 10, 13, 14, 17 and 20 or the samples coded 1, 2, 5, 8, 11, 12, 15, 16, 18 and 19 intranasally as described above for the virus inoculum. Each subject was assigned three bottles labeled with the subject number and randomly distributed such that the group of 20 volunteers were randomly assigned to the bottles coded 3, 4, 6, 7, 9, 10, 13, 14, 17 and 20 (10 subjects) or the bottles coded 1, 2, 5, 8, 11, 12, 15, 16, 18 and 19 (10 subjects). No other medication was permitted during the study.

Whole clotted blood (10 ml) and nasal washing samples were collected on days minus 2, and plus 8, 14, 21, and 28 post-challenge. Nasal secretions were obtained by instilling normal saline into each nostril and collecting the effluent. Naso-pharyngeal swabs for virus isolation were obtained once a day from day minus 2 through day 10 and on day 14 post-challenge.

Serum antibody levels and nasal virus isolation results as well as clinical symptom scores appear in the following Table:

TABLE V

| Subject No. | Test Medication | Sequential Antibody Titers | Virus Isolation From Nasal Washings | Clinical Symptom Scores** |
|---|---|---|---|---|
| 3 | Medication* | <2 | + | 0 |
| | | <2 | | |
| | | <2 | | |
| | | <2 | | |

TABLE V-continued

| Subject No. | Test Medication | Sequential Antibody Titers | Virus Isolation From Nasal Washings | Clinical Symptom Scores** |
|---|---|---|---|---|
| 4 | Medication | <2<br><2<br><2<br><2<br><2 | + | 11 |
| 6 | Medication | <2<br><2 | 0 | 2 |
| 7 | Medication | <2<br><2<br><2<br><2 | 0 | 4 |
| 9 | Medication | <2<br>2<br>2<br>32 | 0 | 3 |
| 10 | Medication | 32<br><2<br><2<br>32<br>32 | 0 | 4 |
| 13 | Medication | <2<br><2<br>≧64 | + | 5 |
| 14 | Medication | <2<br><2<br>≧64<br>≧64 | + | 6 |
| 17 | Medication | 4<br>8<br>≧64<br>≧64 | + | 1 |
| 20 | Medication | 2<br>32<br>≧64<br>≧64 | + | 4 |
| 1 | Placebo | <2<br><2<br>≧64<br>≧64 | + | 43 |
| 2 | Placebo | ≧64<br>≧64<br>≧64<br>≧64 | + | 13 |
| 5 | Placebo | <2<br><2<br><2<br><2 | 0 | 3 |
| 8 | Placebo | <2<br>2<br>32 | 0 | 3 |
| 11 | Placebo | <2<br><2<br>8<br>8<br>≧64 | + | 52 |
| 12 | Placebo | <2<br><2<br>≧64<br>≧64<br>≧64 | + | 16 |
| 15 | Placebo | ≧64<br>≧64<br>≧64<br>≧64 | 0 | 1 |
| 16 | Placebo | 4<br>4<br>4<br>8<br>8 | 0 | 2 |
| 18 | Placebo | <2<br><2<br>≧64<br>≧64 | + | 39 |
| 19 | Placebo | <2<br><2<br><2<br>32<br>32 | + | 64 |

*Test samples containing 1-(4-phenyl-2-thiazolyl)-3-phenylguanidine as hereinabove described.
**The various signs and symptoms of a cold are recorded on a scale of 0 for not present to +3 for severe.

The results of this test show that the compound 1-(4-phenyl-2-thiazolyl)-3-phenylguanidine is effective in protecting humans from rhinovirus type 32 infection as evidenced by the clinical observation that 9 of 10 volunteers receiving 1-(4-phenyl-2-thiazolyl)-3-phenylguanidine did not develop rhinovirus infection from challenge with rhinovirus type 32 while only 4 of 10 volunteers receiving placebo did not develop rhinovirus infection from challenge with the same rhinovirus.

Further, neutralization tests for antibody titer to rhinovirus type 32 challenge supported clinical results in that the subject who received 1-(4-phenyl-2-thiazolyl)-3-phenylguanidine and become clinically infected had no antibody response while the six subjects who received placebo and became clinically infected all had 1:32 or higher antibody titure to rhinovirus type 32.

SPECIFIC EXAMPLES

The following examples described in detail the preparation of representative compounds of the invention.

EXAMPLE 1

Preparation of 4-phenyl-2-thiazolecarbamonitrile

A mixture of 20 gm. (117 mmoles) of diethylamine N-cyanourea R. L. McKee and J. D. Thayer, J. Organic Chem. 17, 1494 (1953), 18.2 gm. (117 mmoles) of phenacyl chloride and 90 ml. of methanol is heated to reflux for 15 minutes, during which time everything dissolves and a new solid separates. The mixture is cooled and filtered yielding 19.8 gm. of the product, melting point 177°–179° C. (dark green melt).

EXAMPLE 2

Preparation of 4-(4-chlorophenyl)-2-thiazolecarbamonitrile

The procedure of Example 1 is repeated employing 4-chlorophenacyl chloride in place of phenacyl chloride. The product had a melting point of 173°–176° C. (dark green melt).

EXAMPLE 3

Preparation of 1-(4-phenyl-2-thiazolyl)-3-phenylguanidine

A solution of 19.8 gm. (100 mmoles) of 4-phenyl-2-thiazolecarbamonitrile and 10 ml. (10.2 gm., 110 mmoles) of aniline in 350 ml. of ethanol is heated to reflux for 8 hours and then cooled overnight to give 23 gm. of product, melting point 179°–180° C. This point is recrystallized from 550 ml. of ethanol to give 19.5 g. of product, melting point 180°–181° C.

EXAMPLE 4

Preparation of 1-(4-phenyl-2-thiazolyl)-3-(3-chlorophenyl) guanidine

A solution of 1.6 gm. (8 mmoles) of 4-phenyl-2-thiazolecarbamonitrile and 0.9 ml. (1.1 gm., 8.6 mmoles) of m-chloroaniline in 30 ml. of ethanol is heated to reflux for 30 hours and then cooled overnight to give 0.7 gm. of product. This product is recrystallized from 5 ml. of ethanol to give 0.45 gm. of product, melting point 134°–135° C.

EXAMPLE 5

Preparation of 1-(4-phenyl-thiazolyl)-3-(4-carbomethoxyphenyl)-guanidine

A solution of 2.0 gm. (10 mmoles) of 4-phenyl-2-thiazolecarbamonitrile and 1.65 gm. (11 mmoles) of methyl 4-aminobenzoate in 40 ml. of ethanol is heated to reflux for 30 hours and then cooled overnight to give 0.75 gm. of product. This product is recrystallized from 15 ml. of ethanol to give 0.6 gm. of product, melting point 189°–191° C.

EXAMPLE 6

Preparation of 1-(4-phenyl-2-thiazolyl)-3-(4-fluorophenyl) guanidine

A solution of 2.0 gm. (10 mmoles) of 4-phenyl-2-thiazolecarbamonitrile and 1.24 gm. (10.5 mmoles) of 4-fluoroaniline in 25 ml. of ethanol is heated to reflux for 7 hours and then cooled overnight to give 1.4 gm. of product. This product is recrystallized from 8 ml. of ethanol yielding 1.0 gm. of product, melting point 156°–158° C.

EXAMPLE 7

Preparation of 1-(4-phenyl-2-thiazolyl)-3-(4-carboxyphenyl) guanidine

A solution of 10.0 gm. (50 mmoles) of 4-phenyl-2-thiazolecarbamonitrile and 7.25 gm. (52.5 mmoles) of p-aminobenzoic acid in 125 ml. of ethanol is heated to reflux for 30 hours during which time a solid appears. The mixture is filtered while hot, to give 5.2 gm. of product. This product is recrystallized from 30 ml. of acetic acid and then dried overnight in an Abderhalden pistol at 110° C., to give 5.1 gm. of product; melting point 245°–247° C.

EXAMPLE 8

Preparation of 1-(4-phenyl-2-thiazolyl)-3-(p-tolyl)guanidine

A solution of 10.0 gm. (50 mmoles) of 4-phenyl-2-thiazolecarbamonitrile and 6.0 gm. (55 moles) of p-toluidine in 150 ml. of ethanol is heated to reflux for 7 hours and then cooled overnight to give 11.5 gm. of product. This product is recrystallized from 100 ml. of ethanol to give 9.3 gm. of product, melting point 152°–153° C.

EXAMPLE 9

Preparation of 1-[4-(4-chlorophenyl)-2-thiazolyl-3-(p-tolyl)guanidine]

A solution of 2.4 gm. (10 mmoles) of 4-(4-chlorophenyl)-2-thiazolecarbamonitrile and 1.2 gm. (11 mmoles) of p-toluidine in 30 ml. of ethanol is heated to reflux for 8 hours and then cooled overnight to give 2.7 gm. of product. This product is recrystallized from 50 ml. of ethanol and then from 20 ml. of toluene yielding 1.0 gm. of product, melting point 175°–177° C.

We claim:

1. A method for treating an infection caused by the growth of rhinovirus which comprises administering to man an antirhinoviral effective amount of a compound of the formula:

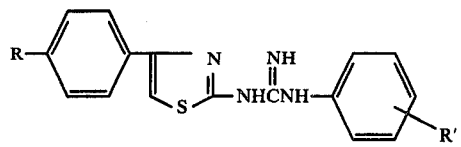

wherein R is selected from the group consisting of hydrogen and chloride; R' is selected from the group consisting of hydrogen, fluoride, chloride, lower alkyl, carboxyl and carboloweralkoxy or a pharmaceutically acceptable acid addition salt thereof.

2. The method according to claim 1 in which the antirhinoviral compound is 1-(4-phenyl-2-thiazolyl)-3-phenylguanidine.

3. The method according to claim 1 wherein the antirhinoviral compound is 1-(4-phenyl-2-thiazolyl)-3-(3-chlorophenyl)guanidine.

4. The method according to claim 1 wherein the antirhinoviral compound is 1-(4-phenyl-2-thiazolyl)-3-(4-carbomethoxyphenyl)guanidine.

5. The method according to claim 1 wherein the antirhinoviral compound is 1-(4-phenyl-2-thiazolyl)-3-(4-fluorophenyl)guanidine.

6. The method according to claim 1 wherein the antirhinoviral compound is 1-(4-phenyl-2-thiazolyl)-3-(4-carboxyphenyl)guanidine.

7. The method according to claim 1 wherein the antirhinoviral compound is 1-(4-phenyl-2-thiazolyl)-3-(p-tolyl)-guanidine.

8. The method according to claim 1 wherein the antirhinoviral compound is 1-[4-chlorophenyl)-2-thiazolyl]-3-(p-tolyl)guanidine.

* * * * *